(12) United States Patent
Kuebler et al.

(10) Patent No.: US 8,506,810 B2
(45) Date of Patent: Aug. 13, 2013

(54) PROCESS AND APPARATUS FOR LOW-EMISSION STORAGE OF BIODEGRADABLE MATTER

(75) Inventors: Hans Kuebler, Munich (DE); Roland Carra, Munich (DE); Margarita Nimmrichter, Hettenshausen (DE)

(73) Assignee: BTA International GmbH, Pfaffenhofen an der Ilm (DE)

( * ) Notice: Subject to any disclaimer, the term of this patent is extended or adjusted under 35 U.S.C. 154(b) by 1355 days.

(21) Appl. No.: 11/577,421

(22) PCT Filed: Oct. 19, 2004

(86) PCT No.: PCT/EP2004/011829
§ 371 (c)(1),
(2), (4) Date: Mar. 3, 2008

(87) PCT Pub. No.: WO2006/042567
PCT Pub. Date: Apr. 27, 2006

(65) Prior Publication Data
US 2008/0263956 A1    Oct. 30, 2008

(51) Int. Cl.
*C02F 3/30*    (2006.01)
*C02F 11/04*    (2006.01)

(52) U.S. Cl.
USPC ............ 210/604; 210/85; 210/151; 210/209; 210/218; 210/259; 210/614; 210/620; 210/630; 366/136

(58) Field of Classification Search
USPC ............ 210/96.1, 150, 151, 198.1, 218, 220, 210/259, 603, 604, 614, 620, 621, 630, 739, 210/85, 205, 209, 605, 631, 806; 366/101, 366/136, 137
See application file for complete search history.

(56) References Cited

U.S. PATENT DOCUMENTS

| | | | | |
|---|---|---|---|---|
| 3,808,123 A | * | 4/1974 | Neel | 210/604 |
| 3,945,916 A | * | 3/1976 | Boulenger | 210/604 |
| 3,980,556 A | * | 9/1976 | Besik | 210/616 |

(Continued)

FOREIGN PATENT DOCUMENTS

| DE | 2415067 A1 | 10/1975 |
|---|---|---|
| DE | 4308920 A1 | 9/1994 |

(Continued)

OTHER PUBLICATIONS

Noike, Characteristics of Carbohydrate Degradation and the Rate-Limiting Step in Anaerobic Digestion, Biotechnology and Bioengineering, vol. XXVII, pp. 1482-1489 (1985), John Wiley & Sons.

*Primary Examiner* — Joseph Drodge
(74) *Attorney, Agent, or Firm* — Chernoff Vilhauer McClung & Stenzel LLP

(57) ABSTRACT

A process and an apparatus for low-emission storage of biodegradable materials by means of aeration, without aerobic conditions materializing in the material, permits a more consistent feed of the downstream stages in the process. Aeration inhibits methanogenesis and the risk potential of an explosive gas mixture forming in the storage vessel or in the components of the system exhausting waste gas. Closed loop control of the aeration adapts the rate of aeration to the biological activity in the stored material and minimizes air input so as to minimize the loss of methanogenesis potential by aerobic conversion of the matter whilst minimizing the energy required for aeration. The process is characterized in that controlling the aeration in the storage vessel inhibits relevant methanogenesis.

13 Claims, 8 Drawing Sheets

(56) References Cited

U.S. PATENT DOCUMENTS

| | | | |
|---|---|---|---|
| 3,994,802 A * | 11/1976 | Casey et al. | 210/605 |
| 4,173,531 A * | 11/1979 | Matsch et al. | 210/624 |
| 4,246,099 A * | 1/1981 | Gould et al. | 210/603 |
| 4,824,571 A * | 4/1989 | Ducellier et al. | 210/603 |
| 5,377,917 A | 1/1995 | Wiljan | |
| 5,906,746 A * | 5/1999 | Helmo et al. | 210/614 |
| 6,015,496 A * | 1/2000 | Khudenko | 210/603 |
| 6,660,164 B1 | 12/2003 | Stover | |
| 6,929,744 B2 | 8/2005 | Le | |
| 7,005,068 B2 * | 2/2006 | Hoffland | 210/603 |

FOREIGN PATENT DOCUMENTS

| | | |
|---|---|---|
| DE | 19833776 | 2/2000 |
| DE | 19907908 | 9/2000 |
| EP | 0038017 A | 10/1981 |
| EP | 0090754 A | 10/1983 |
| WO | 2004 035508 A | 4/2004 |

\* cited by examiner

PROCESS AND APPARATUS FOR LOW-EMISSION STORAGE OF BIODEGRADABLE MATTER

TECHNICAL FIELD

The present invention relates to low-emission storage of biodegradable materials by means of aeration without aerobic conditions materializing in the material, whereby the aeration rate is adapted to the biological activity in the material for storage so that no methane is emitted.

BACKGROUND OF THE ART

Due to their usage or their environmental exposure biodegradable materials often contain a sufficiently versatile biocenosis of microorganisms which biologically degrade these materials completely or partly, depending on the environment concerned, meaning that biodegradation spontaneously materializes in digestion of these materials. This applies especially for wastes having a relevant content of the biogenic-organic materials containing, simply from their origin, a corresponding concentration of microorganisms.

Where an adequate supply of oxygen exists, the carbon bound in the organic substance is converted into cell mass and carbon dioxide, these products corresponding to the natural products of metabolism in the earth's atmosphere. If, however, the oxygen supply is insufficient to ensure aerobic conditions, anaerobic biodegradable processes occur which ultimately can result in methane being generated. When this happens, methane is emitted in open storage of the matter, a gas which in the ambient air poses a relevant danger of explosion and has a high greenhouse potential. This is why storage vessels holding biologically active materials are covered and means for collecting and treating the waste gases connected, or in the case of mixed wastes containing water the material is anaerobically digested in achieving a controlled methanogenesis.

It is often the case that biodegradable materials occur discontinually or are conditioned batchwise in making use of them biologically. For an optimum or steady feed of the downstream bioreactors, buffering the materials is consequently necessary. When subsequently treated aerobically, aerated storage of materials materializes automatically. But if the material is to be digested anaerobically, storage with exclusion of air is obvious, since aerobic storage uses a lot of energy for aerating the materials, resulting in a relevant conversion of potentially methanogenic substances into carbon dioxide.

When the material is anaerobically stored, the anaerobic biodegradable material is subjected to a chain of degrading reactions. Where organic solids are concerned, this chain involves hydrolysis of the solids, acidification of the dissolved intermediate products (acidogenesis), conversion of the resulting acids into acetic acid, hydrogen and carbon dioxide (acetogenesis) ending in the formation of methane (methanogenesis). Responsible for each step in this conversion are certain groups of microorganisms in each case. When this chain of interdependent reactions is balanced, i.e. when the conversion rates of each step in the reaction are equal, the products of a partial step are further made use of in subsequent steps and there is no accumulation of intermediate products, as a result of which the biodegradable organic carbon is converted into methane and carbon dioxide.

However, the various activities involved in the groups of microorganisms may also result in enrichment of intermediate products, it being mostly the case that the spontaneous anaerobic degrading of dissolved biodegradable substances results in enrichment of organic acids in the substrate, since the activity of acidogenic microorganisms is significantly higher than that of methanogenous substances. When the quantity of enriched organic acids exhausts the buffer capacity, the result is a drop in the pH which in turn results in a reduction in the activity of methanogenic microorganisms. The result of this imbalance is an acidified material the low pH of which totally inhibits methanogenesis, a typical example for this stabilizing process being silage from grass cuttings in agriculture.

This self-inhibition of a completely anaerobic biodegradation of biodegradable organic materials comes up against its limits, however, when the biodegradable material in the substrate mix exists mainly particulate and insoluble, with a low potential of readily acidifiable components, a high buffer capacity and when the density of methanogenic microorganisms is elevated. When this is the case, the resulting organic acids are buffered and there is no significant drop in the pH of the substrate mix, resulting in the methanogenic activity being maintained and hydrolysis being the step determining the rate in anaerobic biodegradation (Noike et al. (1985): Characteristics of Carbohydrate Degradation and the Rate-Limiting Step in anaerobic Digestion, Biotechnology and Bioengineering 27, pp 1482-1489).

In actual practice such conditions exist, for example, in anaerobic digestion of biowastes from selective wastes collection. Depending on the time of year involved these wastes feature a relative low percentage of soluble, readily digestable organic matter but a considerable percentage of particulate biomass (e.g. garden waste). Furthermore, wastes of this kind are often mashed with process water before digestion (EP 0 520 172, DE 198 33 776, DE 199 07 908). This process water is preferably obtained from dewatering digested waste, it thus containing both an elevated density of methanogenic microorganisms and a high buffer capacity. The buffer capacity materializes in the digestion of the methane itself from formation of hydrocarbonates, mainly ammonium hydrocarbonate. TAC values of 4 to 8 g/l are often found in the process water. In anaerobic storage of the suspension the result of this is the spontaneous formation of organic acids being too weak to substantially lower the pH and the methanogenic activity from the process water is sufficient to convert organic acids formed as a result of the solids hydrolysis into methane. Methane and carbon dioxide are thus generated in the storage tank from part of the organic carbon.

When methane is formed in storage of the suspension, connecting the bioreactor to a means for collecting biogas is an obvious process solution, as disclosed in EP 1 280 738. The drawback in this aspect is, however, that by connecting the storage vessel to the biogas collection system the fluctuations in the quality of the biogas become even more pronounced. The biogas formed in the storage vessel is characterized by a low content of methane and a high content of carbon dioxide due to the predominant anaerobic reactions in hydroloysis and acidification. Furthermore, the materials supplied to this storage vessel often feature greatly fluctuating volume flows in brief intervals whilst the storage vessel material is tapped relatively consistently, resulting in heavy fluctuations in the levels in the storage vessel.

When material is supplied to the storage vessel, low-methane biogas is displaced from the reactor into the biogas collection system, resulting in addition to the flow of biogas from the digesters a high volume flow of biogas having a low methane content, causing a brief drop of the methane content in the biogas being produced at the time. On completion of the feed to the storage vessel, the level therein drops and a total collapse in the flow of biogas from the storage vessel may occur, resulting in a strong increase in the methane content in the biogas prompting corresponding fluctuations in the calorific value. Since the systems recycling biogas are designed on the basis of the calorific value of the biogas, such fluctuations in the calorific value disrupt operation in making use of the biogas. This can only be avoided by installing a corresponding large biogas storage capacity which, however, adds to the costs of investment and operation. Furthermore, connecting the storage vessel to the biogas collection system results in a drop in the mean methane content in the biogas and thus a deterioration in quality.

For example, digestion of 70 t of biowaste from the separated collection of domestic waste produces a biogas volume flow of approx. 7,200 m$^3$/d daily. When distributed over the full day this biogas production results in a mean volume flow of 300 m$^3$/h and a methane content of approx. 60% by volume. But conditioning the waste material is done batchwise and the resulting waste suspension is discharged with a volume flow of approx. 160 m$^3$/h into the storage vessel. Because of the displacement this results in an additional biogas flow of 160 m$^3$/h with a methane content of approx. 20% by volume. This in turn briefly results in a biogas volume flow of 460 m$^3$/h with a methane content of approx. 46% by volume, in other words, the calorific value of the biogas drops briefly by almost 25%.

DE 198 33 776 shows the necessity of providing a storage vessel upstream of the digestor but with no indication of how to avoid gas emissions from the storage vessel. Although in EP 1 280 738 connecting the storage vessel to the biogas or digestion gas collection system is described, making such a connection results in trouble in operation, in the absence of a sufficient digestion gas storage volume when making use of the digestion gas, due to the fluctuations in the calorific value.

SUMMARY OF THE INVENTION

Object of the invention is low-emission storage of biodegradable materials, now making it possible to feed downstream steps in the process more consistently. Methanogenesis is inhibited by aeration in thus reducing the risk of an explosive gas mixture forming in the storage vessel or in system waste gas components. Closed loop control of aeration adapts the rate thereof to the biological activity in the stored material so as to minimize inclusion of air in thus minimizing both the loss in methanogenic potential due to aerobic matter conversion and in the energy needed for aeration.

BRIEF DESCRIPTION OF THE DRAWINGS

The invention will now be detained by describing embodiments of the process and example aspects of the apparatus with reference to the drawing in which.

DETAILED DESCRIPTION OF A PREFERRED EMBODIMENT

Figure 1:
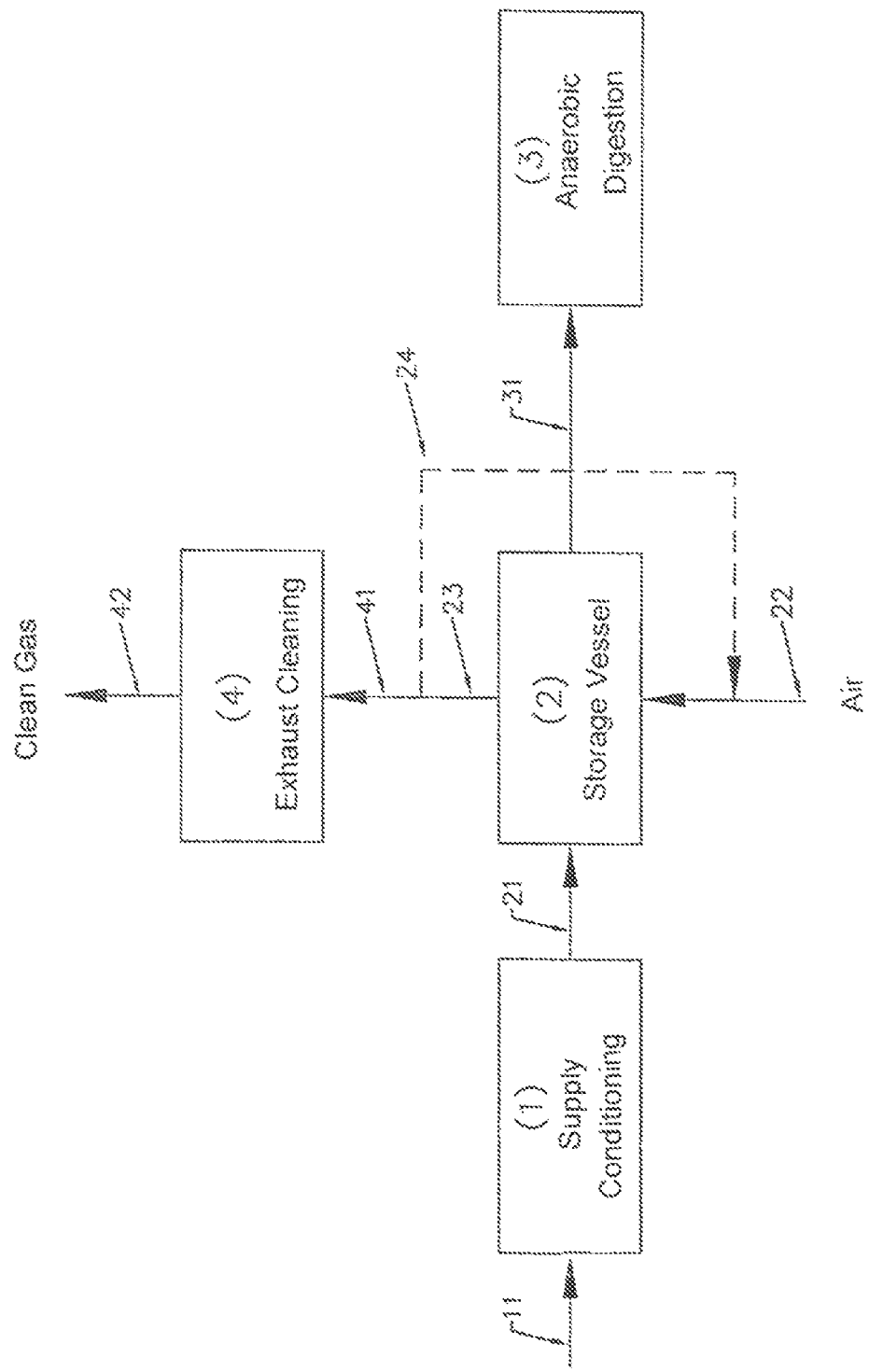
FIG. 1: is a block diagram of how the process in accordance with the invention is managed

Referring now to FIG. 1 there is illustrated how the biodegradable material (11) is made available in a supply zone for treatment in the downstream stages of the process. It is here that any conditioning of the material may be done to ensure smooth operation of the downstream stages of the process. The furnished or also conditioned material (21) is supplied to the storage vessel (2) where it is buffered. Charging the storage vessel (2) with material from the supply or conditioning zone is dictated exclusively by the requirements of the supply or conditioning zone. From the storage vessel (2) the charging (31) of the reactor for anaerobic digestion (3) is activated, discharge of the biodegradable material from the storage vessel (2) being dictated exclusively by the requirements of the digestion stage (3). The storage vessel (2) receives a supply of ambient air (22) to avoid anaerobic storage of the biologically active materials, although instead of ambient air (22) a flow of compressed air or compressed oxygen can be supplied. The air or gases (23) formed by the biological activity in excess are expelled from the storage vessel (2). The waste gas (41) from the storage vessel (2) is supplied to a waste gas scrubber (4) and after cleaning, emitted as clean gas (42). When the waste gas (41) contains no odorous or noxious components it can also be discharged directly.

In a preferred aspect of the process, part of the waste gas (24) from the storage vessel (2) is returned to the storage vessel (2). Returning the partial flow (24) results in a better distribution of the supplied air (22) and an improvement in the transition of the matter by mixing the content of the vessel.

Adapating aeration can be done on the basis of detecting the methane in the waste gas or directly from the gas phase in the vessel either manually or in online-methane detection or by a control algorithm. In detecting the methane in the waste gas or in the gas phase of the storage vessel the aeration is increased incrementally as a function of the increase in the methane concentration. When detecting the methane is zero the rate of aeration is slowly reduced in increments.

Figure 2:
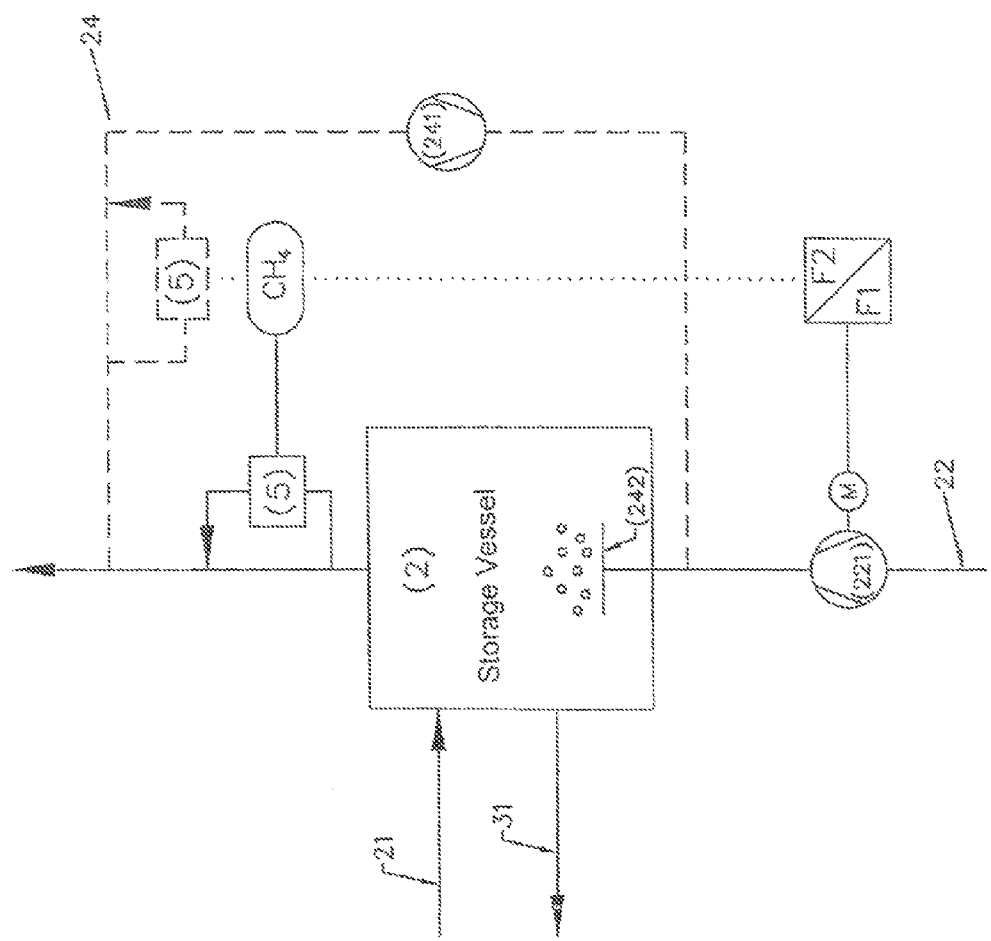
FIG. 2: is a block diagram of process control in accordance with the invention showing how the rate of aeration is controlled

Referring now to FIG. 2 there is illustrated a preferred aspect of the process showing how the rate of aeration is controlled. The storage vessel (2) receives a supply of biodegradable material (21) in accordance with the requirements of the upstream stages in the process. Furthermore, the content of the storage vessel (2) is fed to the downstream stages of the process. A gas (24) is taken from the gas phase of the storage vessel (2) by means of a fan (241) and is returned evenly distributed in the bottom region of the storage vessel (2) by means of the distribution system (242). A further fan (delivery means (221)) feeds air to the storage vessel (2) by the distribution system (242) to avoid anaerobic conditions in the vessel.

In the gas discharge conduit (23) of the storage vessel (2) or in the gas recirculating conduit (24) the methane content of the gas phase of the storage vessel (2) is detected by means of a methane analyzer (5). On the basis of the value detected by the methane analyzer (5) the air delivery of the delivery means (221) is controlled. When the gas analyzer (5) indicates a methane content the delivery of the delivery means (221) is increased until the methane detected has returned to zero. When the reading of the gas analyzer (5) is zero for a predetermined interval, the delivery of the delivery means (221) is gradually reduced until a methane reading is again possible. Subsequently, the delivery of the delivery means (221) is reincreased by a fixed amount. For closed loop control of air delivery by the delivery means (221) as a function of the methane detection in the gas phase a PID or fuzzy controller can be employed.

Figure 3:
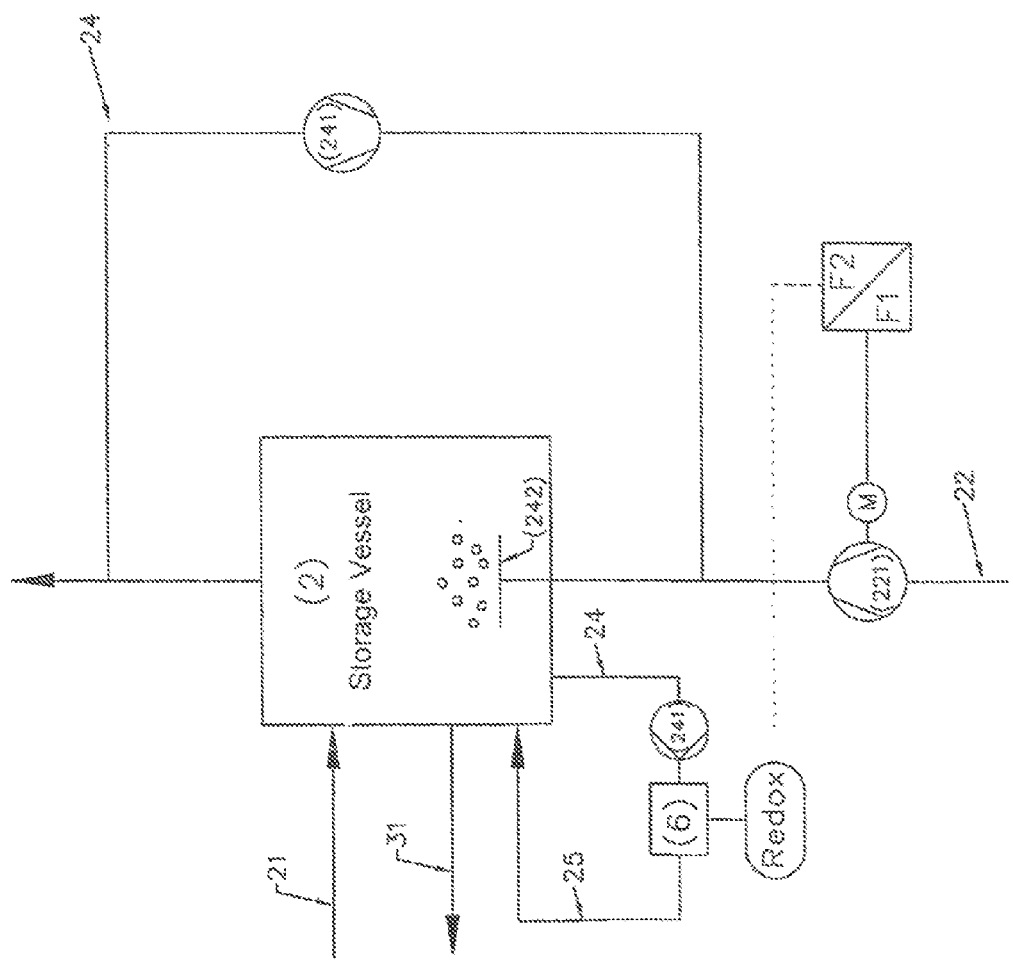
FIG. 3: is a block diagram corresponding to that as shown in FIG. 2 but relating to an alternative embodiment for controlling the rate of aeration

Referring now to FIG. 3 there is illustrated a block diagram showing how setting the aeration can also be done, using the Redox potential as the command variable. By means of a delivery means (241) a partial flow is sampled from the storage vessel (2) and supplied to a Redox analyzer (6). The discharge (25) of the Redox analyzer (6) is returned to the storage vessel (2).

When the Redox potential drops below a preset value the delivery of the delivery means (221) is increased incrementally. When the Redox potential exceeds a preset value the delivery of delivery means (221) is decreased incrementally. In this arrangement, the preset value for the Redox potential is established from values gained from experience for the biodegradable substrate and process controller in each case. Establishing these values can be obtained from lab tests or during the commissioning phase of the technical system. Experience hitherto shows that for an effective control of the aeration the Redox potential should be in the preset value range of −220 to 0 mV.

Figure 4:
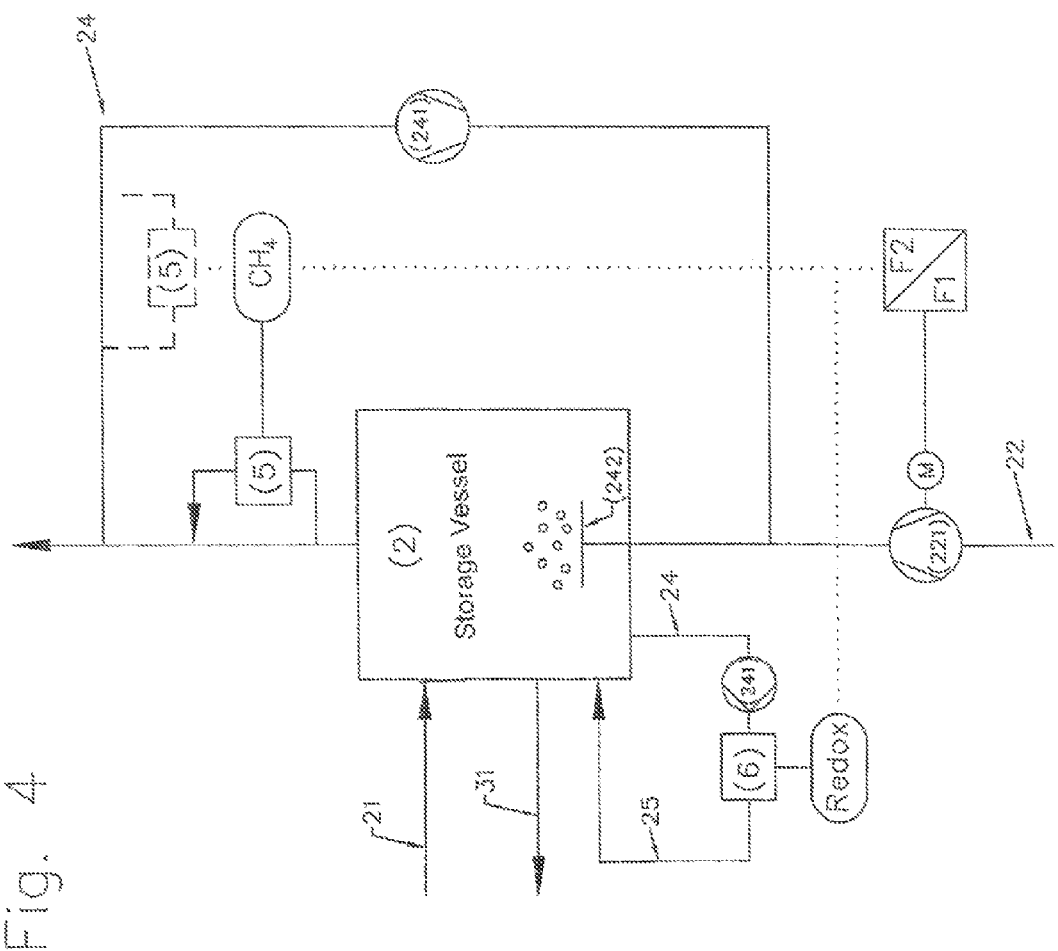
FIG. 4: is a block diagram corresponding to that as shown in FIG. 2 but relating to another alternative embodiment for controlling the rate of aeration

Referring now to FIG. 4 there is illustrated how for controlling the aeration even more precisely the methane content can be detected in the gas phase in combination with detecting the Redox potential of the storage vessel content. In this case, the air delivery of the delivery means (221) is controlled as a function of the deviation of the Redox potential from the preset value as a function of the increase in the methane content. When the analysis with both instruments indicates the preset value being exceeded, the delivery of the delivery means (221) is increased further. Increasing the delivery of delivery means (221) is adapted on the basis of the change in the Redox potential and methane content. When the Redox potential exceeds the preset value and no methane is detected in the gas phase of the storage vessel, the delivery of delivery means (221) is reduced incrementally as a function of the change in the Redox potential.

The results of tests obtained from the storage of pulps of organic wastes show how effective aeration is in reducing formation of the greenhouse gas methane. In these tests an aerated and a non-aerated storage vessel were operated in parallel and the available methane content determined in the waste gas during the storage duration of the individual batches. The results of these tests are shown in the following Table, making it clear that as of an adequate aeration the methane content detected in the waste gas had dropped to zero.

The Redox potential values obtained in the aerated storage vessel indicated a correlation between methanogenesis and Redox voltage. Increasing the Redox voltage results in a reduction in the methanogenesis rate. At Redox voltages exceeding approx. −100 mV methane gas production in testing was zero.

Figure 5:
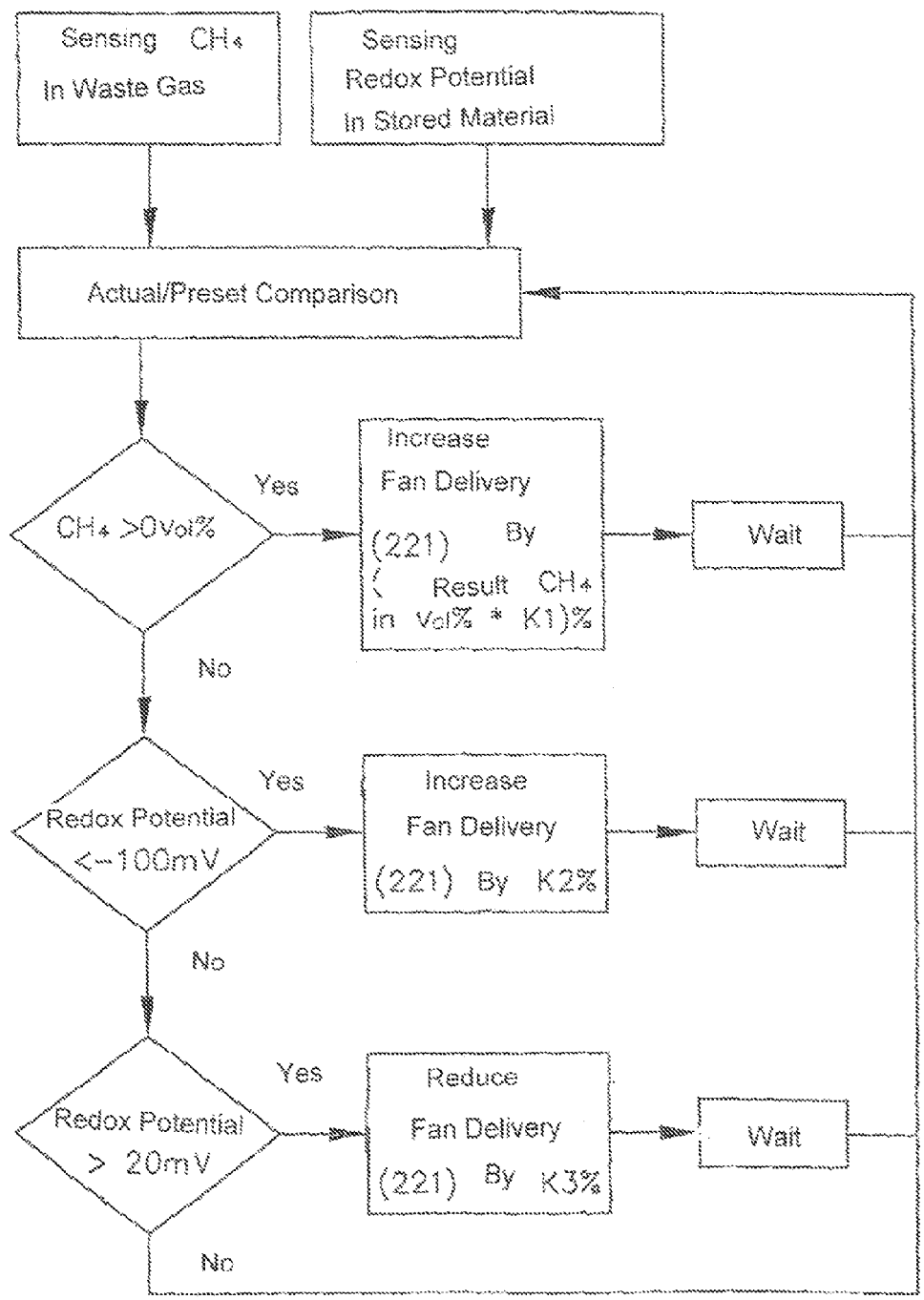
FIG. 5: is a block diagram of an example of a process controller in managing the process in accordance with the invention

Referring now to FIG. 5 there is illustrated an example of an algorithm for controlling a process as managed in accordance with the invention. For controlling the delivery of the delivery means (221) the results of a gas analyzer for determining the methane content in the waste gas of the storage vessel and of a means for determining the Redox potential in the stored material are available. The control algorithm is structured as follows:

1. If methane is detected in the waste gas of the storage vessel, the delivery of the delivery means (221) is increased by a predetermined percentage. This percentage is defined as the product of the detected methane value and a constant K1. After a predetermined waiting period the actual/preset value comparison is repeated.
2. If no methane is detected in the waste gas of the storage vessel the Redox potential is sensed. If this is below −100 mV there is a risk of methanogenesis. This is why the delivery of the delivery means (221) is increased by a predetermined percentage K2 and after a predetermined waiting period the actual/preset value comparison is repeated.
3. If the Redox potential exceeds −20 mV the aeration rate of the stored material is unnecessarily high and the delivery of the delivery means (221) can be reduced by a predetermined percentage K3. After a predetermined waiting period the actual/preset value comparison is repeated.
4. If no methane is detected in the waste gas of the storage vessel and the Redox potential of the stored material is in the range −100 and −20 mV, the actual/preset value comparison is repeated.

Figure 6:
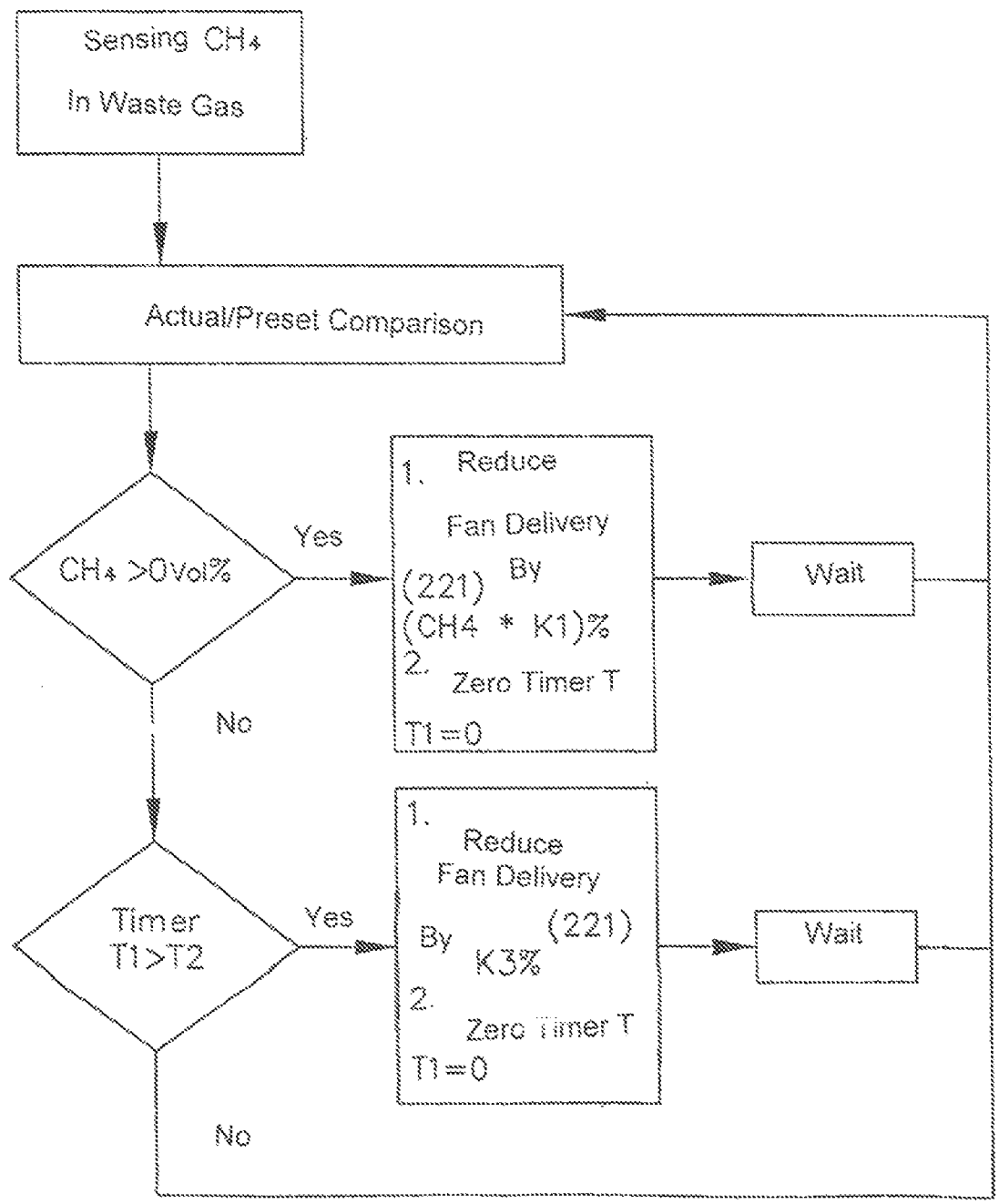
FIG. 6: is a block diagram showing a simplified process controller

Referring now to FIG. 6 there is illustrated the algorithm of a simplified controller based exclusively on detecting methane in the waste gas of the storage vessel.

1. When methane is detected in the waste gas of the storage vessel, then:
   I. the delivery of the fan (221) is increased by a predetermined percentage. This percentage is defined as the product of the detected methane value and a constant K1. On timeout of a predetermined waiting period the actual/preset value comparison is repeated.
   II. The timer T is reset to zero.
On timeout of a predetermined waiting period the actual/preset value comparison is repeated.
2. If no methane is detected in the waste gas of the storage vessel the time T1 of the timer T is checked. If T1 is greater than the critical time T2, the aeration of the stored material is unnecessarily high and

| Aerated storage vessel | | | Non-aerated storage vessel | | |
| --- | --- | --- | --- | --- | --- |
| Aeration rate [l/(h × kg DM)] | Waste gas flow [l] | CH$_4$ in waste gas [vol %] | Aeration rate [l/(h × kg DM)] | Waste gas flow [l] | CH$_4$ in waste gas [vol %] |
| 1.7 | 17.4 | 5.0 | 0 | 11.7 | 18.4 |
| 3.0 | 15.5 | 2.5 | 0 | 13.7 | 12.6 |
| 6.3 | 18.2 | 0.0 | 0 | 15.6 | Unknown |
| 8.1 | 15.9 | 0.0 | 0 | 11.1 | 11.1 |

DM = dry mass of storage material

I. the delivery of the fan (221) is reduced by a predetermined percentage K3 and II. the timer T is reset to zero.

On timeout of a predetermined waiting period the actual/preset value comparison is repeated.

3. If no methane is detected in the waste gas of the storage vessel and if the T1 is smaller than the critical time T2 the actual/preset value comparison is repeated.

EXAMPLE EMBODIMENTS

Example 1

Figure 7:
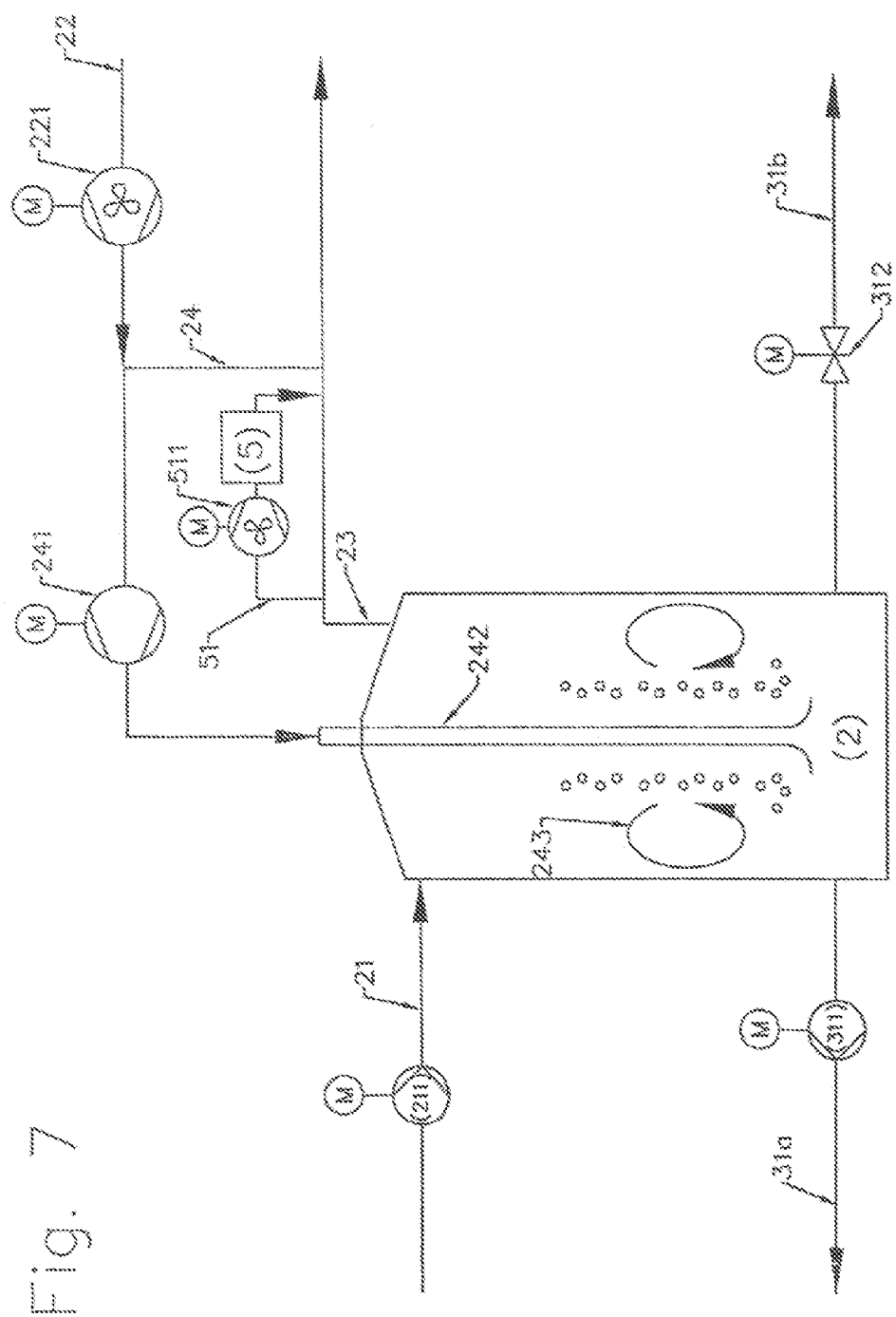
FIG. 7: is an illustration of a preferred aspect

Referring now to FIG. 7 there is illustrated a preferred embodiment of the apparatus in accordance with the invention for pumping the inflow (21) and outflow (31a) of the material is pumped when the storage material is pumpable. For this purpose centrifugal or displacement pumps (211; 311) can be employed depending on the integration hydraulically. As an alternative, the outflow may also be activated by means of a final control element (312) in gravity flow (31b). To circulate the content of the storage vessel (2) a partial flow is sampled from the exhaust flow (23) and entered into the stored material by means of a compressor (241; e.g. positive displacement compressor) via a lance system (242) located centrally above the middle of the floor of the vessel. The rising gas bubbles create a strong loop flow (243) ensuring a thorough intermixing of the vessel contents. A lance system with its top feed has the advantage that when the lance system is in need of repair, the vessel does not need to be emptied, but instead, the lance system removed from the top of the vessel. At the suction end of the compressor (241) a blower (221) e.g. fan) transports the required air 22 into the circulating gas flow. A further blower (511) e.g. fan) samples from the exhaust air flow (23) a further partial flow and feeds it to a methane analyzer (5; e.g. infrared absorption analyzer).

Figure 8:
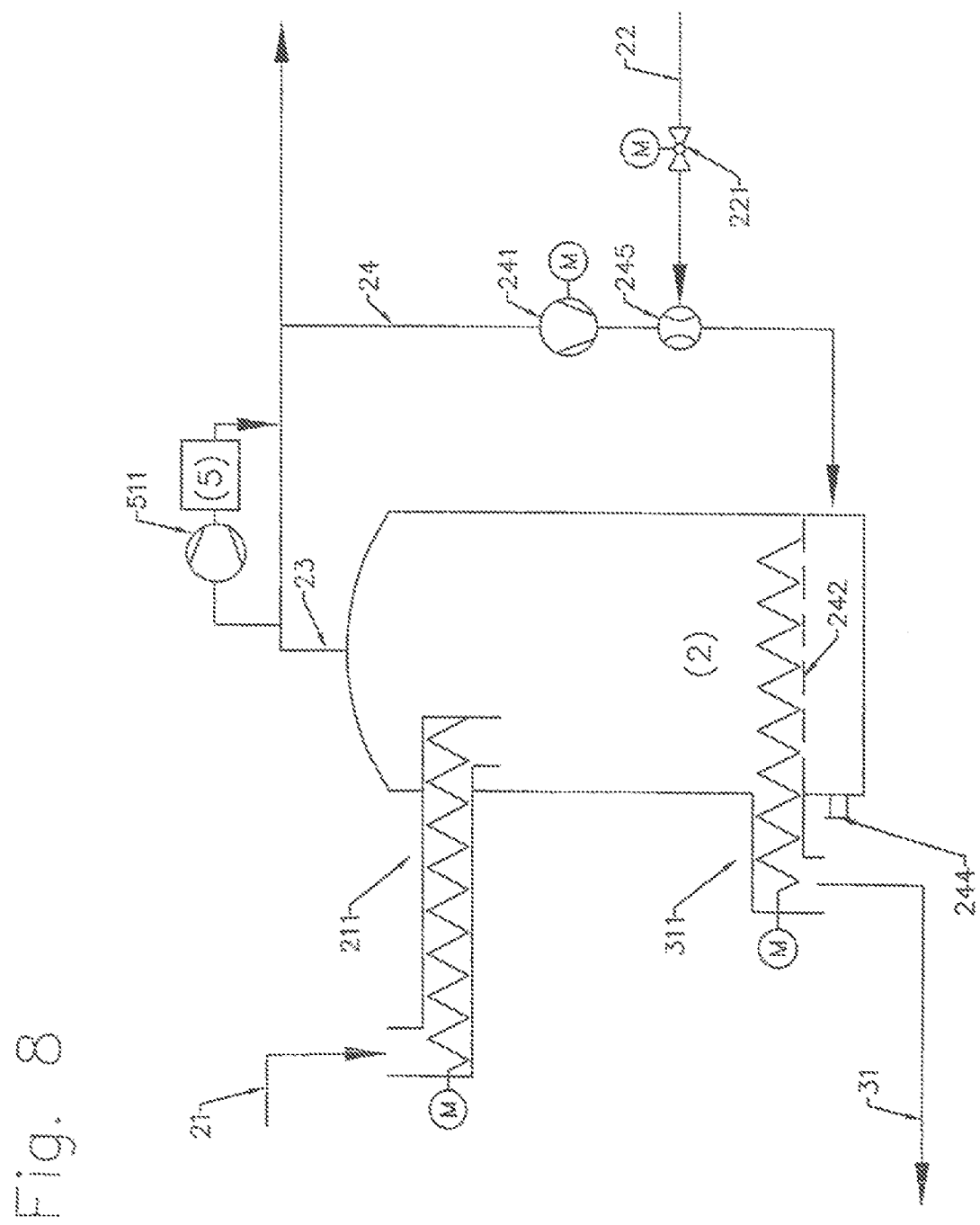
FIG. 8: is an illustration of a further preferred aspect.

Referring now to FIG. 8 there is illustrated a preferred embodiment of the apparatus in accordance with the invention showing how a screw conveyor (211; 311) is used to handle inflow (21) and outflow (31) of the material. For aerating the content of the storage vessel (2) a partial flow is sampled from the exhaust flow (23) and returned to the vessel by means of a delivery assembly (241: e.g. rotary spool valve). Aeration occurs via a slotted or perforated tray (242) at the bottom of the storage vessel (2) over which the discharge screws run, the flow thereof being crosswise to the slotted tray to prevent the latter from becoming clogged up. Provided below the slotted tray in the vessel is a maintenance port (244) permitting maintenance of the slotted tray as well as removal of material having fallen therethrough. Provided at the pressure end of the delivery assembly (241) is a nozzle or aperture (245) via the vacuum zone of which ambient air (22) can be aspirated. By means of a final control element (221) in the air intake conduit the incoming air flow can be varied. A blower (511; e.g. fan) samples from the exhaust air flow (23) a further partial flow and feeds it to a methane analyzer (5 e.g. thermal conductivity analyzer).

Advantages:

The process in accordance with the invention permits cost-effective, low-emission storage of biodegradable materials. Inhibiting methanogenesis makes for the following improvements:

The storage vessel now permits a more consistent charging of the downstream stages in the process which in turn achieves longer running periods of the apparatus and smaller thruputs as well as a more consistent production of biogas. Furthermore, the storage vessel no longer needs to be connected to the biogas collection of a downstream digester in thus significantly reducing fluctuations of the methane content in the biogas whilst increasing the mean methane content. Both of these factors enhance the efficiency of a process stage for recycling biogas whilst minimizing the biogas storage volume required with all the economic advantages of: lower costs for biogas storage and recycling, since its production is now more consistent, together with higher efficiency in recycling the biogas since its quality is more consistent.

Closed loop control of the aeration minimizes the air intake in thus minimizing the loss of methanogenesis potential by conversion of the aerobic matter as well as the energy required for aeration in ensuring maximum energy yield from a downstream stage for anaerobic digestion.

The risk potential of an explosive gas mixture forming in the storage vessel or in the exhaust components of the system is now reduced, resulting in a reduction in the costs for system safeguards.

Since the storage vessel can now be decoupled from the biogas collection system the components handling biogas in the system and thus the explosion protection zones are reduced.

The invention claimed is:

1. A method of processing biodegradable material, comprising:
supplying the biodegradable material to a storage vessel for buffering therein,
removing waste gas generated in the storage vessel,
mixing at least some of the removed waste gas with an oxygen-containing gas,
aerating the biodegradable material in the storage vessel by supplying at least some of the mixture of waste gas and oxygen-containing gas to the storage vessel, whereby biological activity of the biodegradable material is modified in a manner such as to inhibit at least one of methanogenesis and formation of an explosive gas mixture in the storage vessel, and
supplying the biodegradable material from the storage vessel to a biogas reactor for anaerobic digestion to generate biogas by means of hydrolysis, acetogenesis and methanogenesis.

2. The process as set forth in claim 1, wherein the mixing step comprises mixing waste gas with ambient air.

3. The process as set forth in claim 1, comprising detecting methane content in the waste gas removed from the storage vessel or in the waste gas returned to the storage vessel and activating a closed loop control of aeration of the storage vessel depending on detection of methane content.

4. The process as set forth in claim 3, comprising detecting the methane content by means of infrared absorption or thermal conductivity.

5. The process as set forth in claim 1, comprising sensing the Redox potential of biodegradable material in the storage vessel and activating a closed loop control of aeration of the storage vessel depending on the sensed Redox potential.

6. The process as set forth in claim 5, comprising maintaining the Redox potential of the storage medium in the range −220 to 0 mV.

7. The process as set forth in claim 1, comprising detecting methane content in the waste gas removed from the storage vessel or in the waste gas returned to the storage vessel, sensing the Redox potential of biodegradable material in the storage vessel, and activating a closed loop control of aeration of the storage vessel depending on detection of methane content and on the sensed Redox potential.

8. A method of processing biodegradable material, comprising:

supplying the biodegradable material to a conditioning zone, conditioning the biodegradable material in the conditioning zone to prepare the biodegradable material for anaerobic digestion, supplying the biodegradable material from the conditioning zone to a storage vessel for buffering therein, removing waste gas generated in the storage vessel, mixing at least some of the removed waste gas with an oxygen-containing gas;

aerating the biodegradable material in the storage vessel by supplying at least some of the mixture of waste gas and oxygen-containing gas to the storage vessel, whereby biological activity of the biodegradable material is modified in a manner such as to inhibit at least one of methanogenesis and formation of an explosive gas mixture in the storage vessel, and supplying the biodegradable material from the storage vessel to a biogas reactor for anaerobic digestion to generate biogas by means of hydrolysis, acetogenesis and methanogenesis, wherein the biodegradable material is supplied to the storage vessel exclusively in accordance with requirements of the conditioning zone and the biodegradable material is supplied to the biogas reactor exclusively in accordance with requirements of the biogas reactor.

9. An apparatus for implementing the method according to claim 1, comprising:

a biogas reactor for anaerobic digestion of biodegradable material to generate biogas by means of hydrolysis, acetogenesis and methanogenesis, a storage vessel upstream of the bioreactor for buffering biodegradable material before the biodegradable material is supplied to the biogas reactor, the storage vessel having a waste gas outlet and an aerating gas inlet, and ducting connected to the storage vessel and to a source of oxygen-containing gas for removing waste gas generated in the storage vessel via the waste gas outlet, mixing at least some of the removed waste gas with oxygen-containing gas from said source, and supplying at least some of the mixture of waste gas and oxygen-containing gas to the storage vessel via the aerating gas inlet for aerating the biodegradable material in the storage vessel.

10. The apparatus as set forth in claim 9, wherein the source of oxygen-containing gas comprises a compressed air delivery system.

11. The apparatus as set forth in claim 9, wherein the source of oxygen-containing gas comprises a source of compressed oxygen.

12. The apparatus as set forth in claim 9, comprising a gas distribution structure for distributing the oxygen-containing gas flow in the biodegradable material in the storage vessel.

13. The apparatus as set forth in claim 9, comprising a duct for diverting a sample of the waste gas removed from the storage vessel and a methane analyzer connected to said duct for receiving said sample.

\* \* \* \* \*